United States Patent
Sun, Jr. et al.

(10) Patent No.: US 9,032,719 B2
(45) Date of Patent: May 19, 2015

(54) PARTICULATE FILTER PERFORMANCE MONITORING

(71) Applicant: GM Global Technology Operations LLC, Detroit, MI (US)

(72) Inventors: Min Sun, Jr., Troy, MI (US); Michelangelo Ardanese, Royal Oak, MI (US); Vincent J. Tylutki, Livonia, MI (US); Igor Anilovich, Walled Lake, MI (US)

(73) Assignee: GM Global Technology Operations LLC, Detroit, MI (US)

(*) Notice: Subject to any disclaimer, the term of this patent is extended or adjusted under 35 U.S.C. 154(b) by 34 days.

(21) Appl. No.: 13/943,142

(22) Filed: Jul. 16, 2013

(65) Prior Publication Data
US 2015/0020507 A1 Jan. 22, 2015

(51) Int. Cl.
*F01N 3/02* (2006.01)
*F01N 11/00* (2006.01)
*F01N 3/021* (2006.01)
*G01M 15/10* (2006.01)
*G01N 15/08* (2006.01)

(52) U.S. Cl.
CPC ............. *F01N 11/00* (2013.01); *F01N 3/021* (2013.01); *G01M 15/102* (2013.01); *G01N 15/08* (2013.01)

(58) Field of Classification Search
CPC ...... F01N 9/002; F01N 11/00; F01N 2550/04; Y02T 10/47
USPC ...................................................... 60/272–324
See application file for complete search history.

(56) References Cited

U.S. PATENT DOCUMENTS

| | | | |
|---|---|---|---|
| 6,432,168 B2 * | 8/2002 | Schonauer | 95/18 |
| 8,561,388 B2 * | 10/2013 | Yahata et al. | 60/277 |
| 8,656,763 B2 * | 2/2014 | Yoshioka | 73/114.31 |
| 2008/0282682 A1 * | 11/2008 | C. et al. | 60/291 |
| 2012/0117945 A1 * | 5/2012 | Krafthefer et al. | 60/274 |
| 2012/0144813 A1 * | 6/2012 | Yahata et al. | 60/311 |

* cited by examiner

*Primary Examiner* — Jesse Bogue
(74) *Attorney, Agent, or Firm* — Cantor Colburn LLP (57) ABSTRACT

A method for particulate filter performance monitoring in an exhaust gas treatment system is provided. The method includes monitoring a current received from a soot sensor in the exhaust gas treatment system and comparing the current to a soot sensor current threshold. Based on determining that the current is greater than or equal to the soot sensor current threshold, an accumulated engine out soot value is compared to an accumulated engine out soot threshold. A particulate filter fault is set based on determining that the accumulated engine out soot value is less than the accumulated engine out soot threshold. A monitoring system and an exhaust gas treatment system of an engine are also provided.

17 Claims, 5 Drawing Sheets

PARTICULATE FILTER PERFORMANCE MONITORING

FIELD OF THE INVENTION

The subject invention relates to exhaust system monitoring and more specifically to particulate filter performance monitoring in an exhaust system.

BACKGROUND

The emission of particulate matter in exhaust from compression-ignition engines is regulated for environmental reasons. Thus, vehicles equipped with compression-ignition engines often include after-treatment components such as particulate filters, catalyzed soot filters and adsorption catalysts for removing particulate matter and other regulated constituents (e.g., nitrogen oxides or NOx) from their exhaust streams. Particulate filters and other after-treatment components can be effective, but can also increase back pressure as they collect particulate matter.

Particulate matter may include ash and unburned carbon particles generally referred to as soot. As this carbon-based particulate matter accumulates in the after-treatment components, it can increase back pressure in the exhaust system. Engines that have large rates of particulate mass emission can develop excessive back pressure levels in a relatively short period of time, decreasing engine efficiency and power producing capacity. Therefore, it is desired to have particulate filtration systems that minimize back-pressure while effectively capturing particulate matter in the exhaust.

To accomplish both of these competing goals, after-treatment components must be regularly monitored and maintained either by replacing components or by removing the accumulated soot. Cleaning the accumulated soot from an after-treatment component can be achieved via oxidation to $CO_2$ (i.e., burning-off) and is known in the art as regeneration. To avoid service interruptions, regeneration is generally preferred over replacement of after-treatment components.

An engine control system may use a soot model to deduce (i.e., predict) a mass of soot accumulated in the after-treatment component by monitoring properties of the exhaust stream as it flows through the after-treatment component. The control system can use the deduced soot mass data to monitor soot loading over time, to determine or anticipate when regeneration may be necessary or desirable, to facilitate a regeneration event, and/or to effectuate control over a regeneration process or other remedial measures. Soot models typically need to be accurate while accounting for a number of vehicle conditions.

To ensure that after-treatment components are in good operating order, performance monitoring for faults in the after-treatment components is also performed. High accuracy soot and sensor models can be used to determine when a fault condition exists in a particulate filter. Making fault comparisons between multiple models can increase a risk of incorrectly declaring that a fault exists, particularly when performing time-based comparisons. Incorrectly declaring that a fault exists may lead to performance of otherwise unnecessary diagnostic and maintenance operations.

Accordingly, it is desirable to provide systems and methods for monitoring particulate filter performance in an exhaust system that reduces the risk of incorrectly declaring a fault.

SUMMARY OF THE INVENTION

In one exemplary embodiment, a method for particulate filter performance monitoring in an exhaust gas treatment system is provided. The method includes monitoring a current received from a soot sensor in the exhaust gas treatment system and comparing the current to a soot sensor current threshold. Based on determining that the current is greater than or equal to the soot sensor current threshold, an accumulated engine out soot value is compared to an accumulated engine out soot threshold. A particulate filter fault is set based on determining that the accumulated engine out soot value is less than the accumulated engine out soot threshold.

In another exemplary embodiment, a monitoring system for an exhaust gas treatment system is provided. The monitoring system includes a first module configured to monitor a current received from a soot sensor in the exhaust gas treatment system, compare the current to a soot sensor current threshold, and initiate a trigger based on a determination that the current is greater than or equal to the soot sensor current threshold. The monitoring system includes a second module configured to compare an accumulated engine out soot value to an accumulated engine out soot threshold in response to the trigger, and set a particulate filter fault based on a determination that the accumulated engine out soot value is less than the accumulated engine out soot threshold.

In yet another exemplary embodiment, an exhaust gas treatment system of an engine is provided. The exhaust gas treatment system includes a particulate filter, a soot sensor configured to output a current related to an amount of soot over a period of time in an exhaust path downstream of the particulate filter, and a monitoring system. The monitoring system is configured to compare the current to a soot sensor current threshold, initiate a trigger based on a determination that the current is greater than or equal to the soot sensor current threshold, compare an accumulated engine out soot value to an accumulated engine out soot threshold in response to the trigger, and set a particulate filter fault based on a determination that the accumulated engine out soot value is less than the accumulated engine out soot threshold.

The above features and advantages and other features and advantages of the invention are readily apparent from the following detailed description of the invention when taken in connection with the accompanying drawings.

BRIEF DESCRIPTION OF THE DRAWINGS

Other features, advantages and details appear, by way of example only, in the following detailed description of embodiments, the detailed description referring to the drawings in which.

DESCRIPTION OF THE EMBODIMENTS

The following description is merely exemplary in nature and is not intended to limit the present disclosure, its application or uses. It should be understood that throughout the drawings, corresponding reference numerals indicate like or corresponding parts and features.

As used herein, the term "module" refers to processing circuitry that can include an application specific integrated circuit (ASIC), an electronic circuit, a processor (shared, dedicated, or group) and memory that executes one or more software or firmware programs, a combinational logic circuit, and/or other suitable components that provide the described functionality. When implemented in software, a module can be embodied in memory as a non-transitory machine-readable storage medium readable by a processing circuit and storing instructions for execution by the processing circuit for performing a method.

Figure 1:
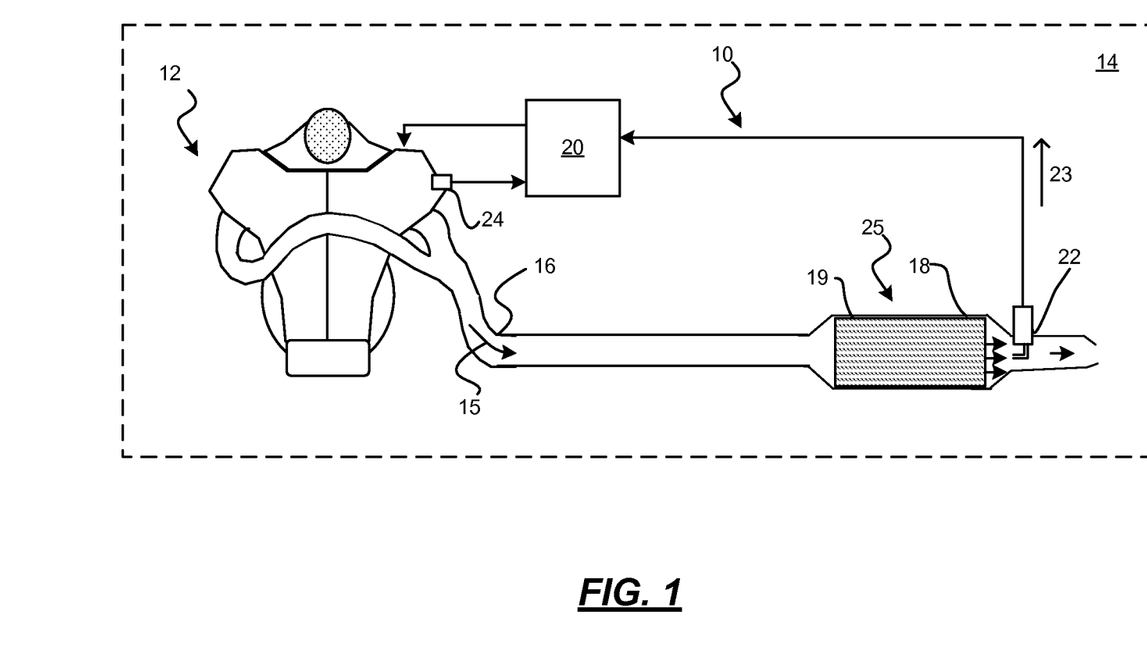
FIG. 1 is a functional block diagram of a vehicle including an exhaust gas treatment system in accordance with exemplary embodiments.

In accordance with an exemplary embodiment of the invention, FIG. 1 depicts an exhaust gas treatment system 10 for the reduction of regulated exhaust gas constituents of an internal combustion engine 12, including an engine of a vehicle 14 as well as engines used in various non-vehicular applications. As can be appreciated, the engine 12 can be of any engine type including, but not limited to, a diesel engine, a gasoline direct injection engine, a homogeneous charge compression ignition engine, or other engine type.

The exhaust gas treatment system 10 generally includes one or more exhaust gas conduits 16, and one or more exhaust treatment devices. In various embodiments, the exhaust treatment devices can include a particulate filter 18 and an oxidation catalyst device, a selective catalytic reduction device, and/or other treatment device (not depicted).

In FIG. 1, the exhaust gas conduit 16, which may comprise several segments, transports exhaust gas 15 from the engine 12 to the various exhaust treatment devices of the exhaust gas treatment system 10. The exhaust treatment devices operate to filter the exhaust gas of emissions and particulate matter. The particulate filter 18, in particular, operates to filter the exhaust gas 15 of soot, including unburned carbon and other particulates. In various embodiments, the particulate filter 18 may be constructed using a wall flow monolith filter media 19 or other filter devices such as wound or packed fiber filters, open cell foams, sintered metal fibers, etc. The filter media 19 may be packaged in a shell or canister that is, for example, stainless steel, and that has an inlet and an outlet in fluid communication with exhaust gas conduit 16.

The accumulated particulate matter within the particulate filter 18 is periodically cleaned by regeneration. Regeneration involves the oxidation or burning of accumulated carbon and other particulates in what is typically a high temperature (>600° C.) environment.

A control module 20 controls the engine 12 and/or one or more exhaust components based on sensed and/or or modeled data. The sensed data can be received from one or more sensors, such as sensor 22 of the exhaust gas treatment system 10. The sensor 22 is configured to collect deposits of soot from the exhaust gas 15 downstream of the particulate filter 18. The sensor 22 outputs an electric current 23 in response to an amount of soot accumulated in the sensor 22. The sensor 22 may operate substantially as a reduced-size particulate filter, and similar to the particulate filter 18, the sensor 22 is subject to regeneration after accumulating an amount of soot. The control module 20 is configured to receive the electric current 23, also referred to as current 23, and determine an amount of soot in the sensor 22 based on a predetermined relationship between soot and current level. The control module 20 also receives engine data from one or more sensors 24 of the engine 12. Data from the one or more sensors 24 of the engine 12 can be sent directly to the control module 20 or may be preprocessed to form various engine parameters prior to being received by the control module 20.

In various embodiments, the control module 20 controls regeneration of the particulate filter 18. For example, the control module 20 monitors various exhaust system parameters and engine parameters to determine when a regeneration event should begin or has completed. The control module 20 can implement an engine out soot model to generate an engine out soot flow rate prediction based on, for example, a measured level of oxides of nitrogen (NOx), an engine timing factor of the engine 12, and an engine air-fuel ratio factor of the engine 12. The engine out soot flow rate prediction provides a model or predicted soot/particulate flow rate out of the engine 12 and into the particulate filter 18. The engine timing factor may be based on engine fuel injection timing of the engine 12. The engine air-fuel ratio factor may be based on an air-fuel ratio of the engine 12. The control module 20 can generate a particulate filter soot loading prediction and an accumulated engine out soot value based on the engine out soot flow rate prediction. The control module 20 may control regeneration of the particulate filter 18 based on the particulate filter soot loading prediction.

The control module 20 also controls regeneration of the sensor 22. The control module 20 may be configured to initiate regeneration of the sensor 22 based on a predetermined limit for the current 23 or an equivalent level of soot in the sensor 22.

Figure 2:
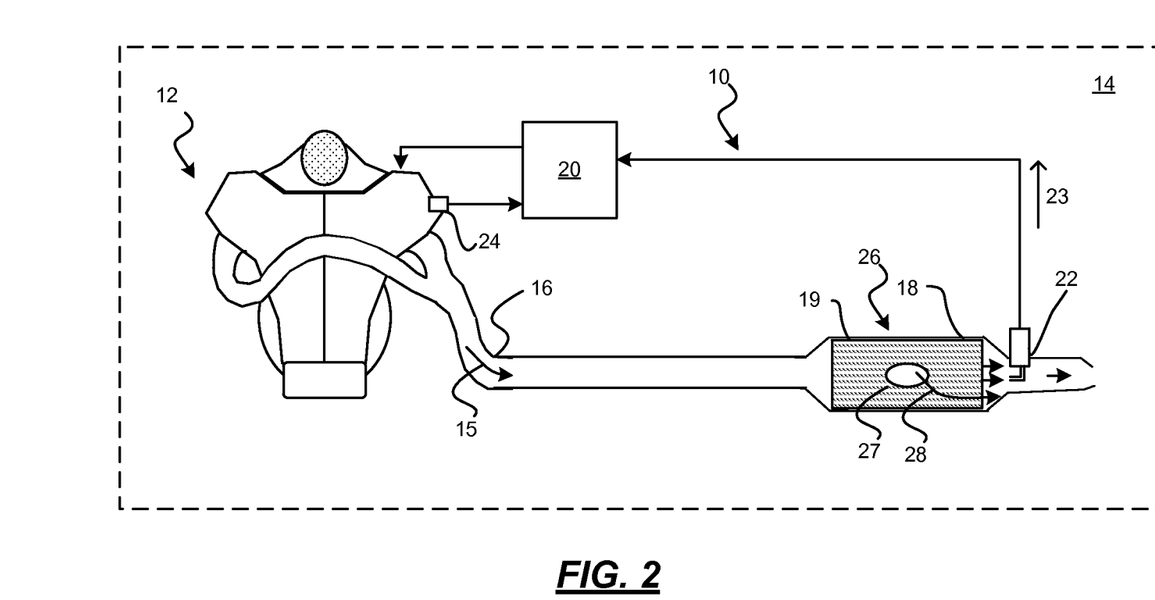
FIG. 2 is a functional block diagram of a vehicle including an exhaust gas treatment system with a modified particulate filter in accordance with exemplary embodiments.

The example of FIG. 1 represents a production version 25 of the particulate filter 18, which is properly sealed and installed in communication with the exhaust gas conduit 16. The example of FIG. 2 is a functional block diagram of the vehicle 14 of FIG. 1 including the exhaust gas treatment system 10, engine 12, one or more exhaust gas conduits 16 for exhaust gas 15, sensor 22 providing current 23 to control module 20, as well as one or more sensors 24 for the engine 12. However, instead of the production version 25 of the particulate filter 18, FIG. 2 includes an emission limit fault version 26 of the particulate filter 18. The emission limit fault version 26 of the particulate filter 18 is a modified particulate filter that includes a crack or hole 27 in the filter media 19 which is sized to cause excessive particulate matter emissions 28. The emission limit fault version 26 of the particulate filter 18 may be intentionally installed for various test procedures to verify that when the particulate filter 18 is sufficiently damaged that an emission limit fault is detected for the particulate filter 18. The crack or hole 27 may be sized to cause about 1.75 times normal particulate matter emissions. Cycles of various test scenarios and procedures, e.g., federal test procedure cycles, may be performed using the emission limit fault version 26 of the particulate filter 18 to verify compliance of the exhaust gas treatment system 10 with emission regulations.

The emission limit fault version 26 of the particulate filter 18 has reduced filter efficiency relative to the production version 25 of the particulate filter 18 of FIG. 1. Accordingly, more soot accumulates in the sensor 22 and less soot accumulates in the emission limit fault version 26 of the particulate filter 18 than in the production version 25 of the particulate filter 18 of FIG. 1 over a given period of time under the same operating conditions.

In exemplary embodiments, the emission limit fault version 26 of the particulate filter 18 is used to establish calibration parameters as thresholds for performance monitoring of the particulate filter 18 such that loss of efficiency or damage to the production version 25 of the particulate filter 18 of FIG. 1 which is substantially similar to or worse than that of the emission limit fault version 26 of the particulate filter 18 can be detected without requiring multiple high accuracy models of the sensor 22 and soot output of the engine 12. Thresholds can be further refined in view of driving profiles. Different driving profiles can be established based on a number of parameters, such as load and power of the engine 12, exhaust temperature of the exhaust gas 15, and the like. For instance, operating the engine 12 at steady-state and low RPM will typically result in a lower rate of soot output from the engine 12 than operating under a greater load and higher RPM.

Figure 3:
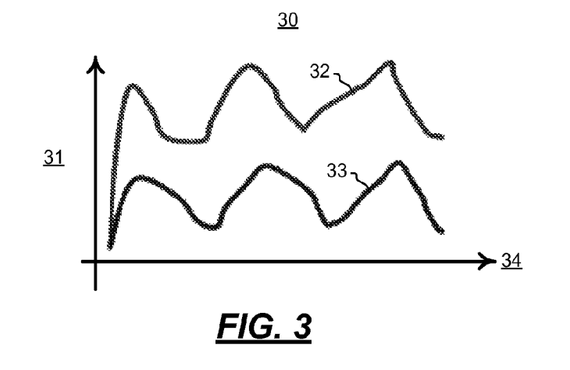
FIG. 3 is an example plot illustrating variations in engine out soot rate between different driving profiles over a period of time.

FIG. 3 is an example plot 30 illustrating variations in engine out soot rate 31 between a pair of driving profiles 32 and 33 over a period of time 34. In FIG. 3, the y-axis is engine out soot rate 31, and the x-axis is time 34. Driving profile 32 indicates a greater load or power condition that results in a higher engine out soot rate 31 over the same period of time 34 as compared to the lower engine out soot rate 31 of driving profile 33.

Figure 4:
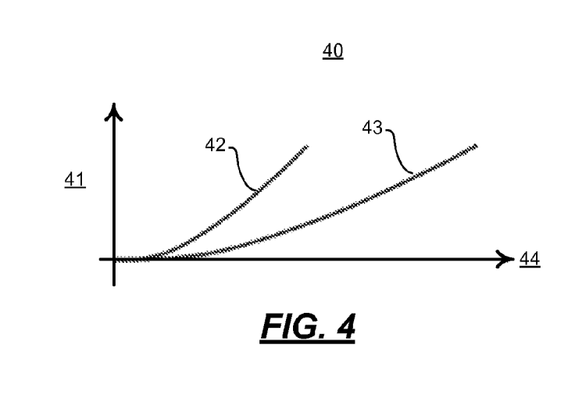
FIG. 4 is an example plot illustrating variations in accumulated engine out soot between different driving profiles over a period of time.

FIG. 4 is an example plot 40 illustrating variations in accumulated engine out soot 41 between a pair of driving profiles 42 and 43 over a period of time 44. In FIG. 34 the y-axis is accumulated engine out soot 41, and the x-axis is time 44. Driving profile 42 corresponds to driving profile 32 of FIG. 3, where a greater load or power condition results in a higher engine out soot rate 31 and thus more rapid growth in accumulated engine out soot 41. Similarly, driving profile 43 corresponds to driving profile 33 of FIG. 3, where a lower load or power condition results in a lower engine out soot rate 31 and thus slower growth in accumulated engine out soot 41 as compared to driving profile 42.

Figure 5:
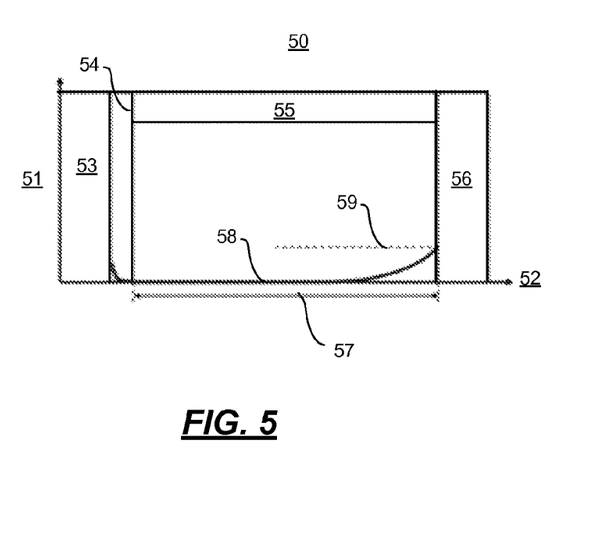
FIG. 5 is an example plot illustrating soot sensor current over a period of time relative to various sensor events.

FIG. 5 is an example plot 50 illustrating soot sensor current 51 over a period of time 52 relative to various events for the sensor 22 of FIGS. 1 and 2. The soot sensor current 51 represents an example of a detected level of the current 23 of FIGS. 1 and 2. The sensor 22 of FIGS. 1 and 2 undergoes regeneration 53 and thermalization 54, followed by deposition of particles 55, and regeneration 56. A period of time 52 for the deposition of particles 55 is referred to as a sensor response time 57. A monitored current 58 remains relatively negligible for most of the sensor response time 57 until a sufficient amount of soot is deposited in the sensor 22 of FIGS. 1 and 2 and a soot sensor current threshold 59 is reached. Upon reaching the soot sensor current threshold 59, regeneration 56 is performed to reset the sensor 22. A value for the soot sensor current threshold 59 may be established by monitoring the current 23 of FIG. 2 while the exhaust gas treatment system 10 includes the emission limit fault version 26 of the particulate filter 18 of FIG. 2 configured to produce a detectable failure during a test procedure cycle. For instance, the soot sensor current threshold 59 may be a maximum current detected during the test procedure cycle.

Figure 6:
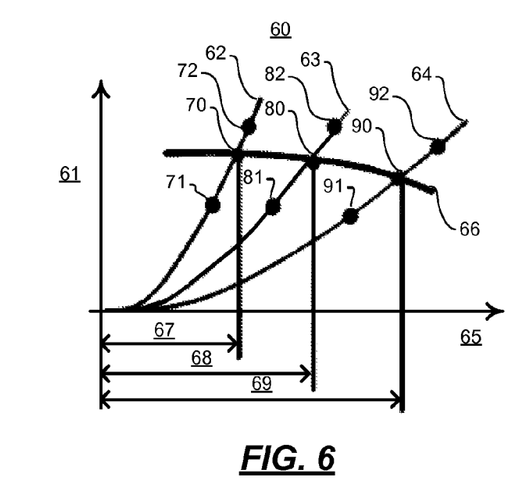
FIG. 6 is an example plot illustrating variations in accumulated engine out soot between different driving profiles over a period of time relative to an accumulated engine out soot threshold.

FIG. 6 is an example plot 60 illustrating variations in accumulated engine out soot 61 between driving profiles 62, 63, and 64 over a period of time 65 relative to an accumulated engine out soot threshold 66. Similar to FIG. 4, the driving profiles 62, 63 and 64 represent relatively lower engine out soot rates resulting in progressively longer response times. In the example of FIG. 6, driving profile 62 has a faster response time 67 as compared to response time 68 of driving profile 63. Driving profile 64 has a slower response time 69 than response time 68 of driving profile 63. The response times 67-69 represent values of the sensor response time 57 where the soot sensor current threshold 59 of FIG. 5 is met under different operating conditions of the engine 12 of FIGS. 1 and 2.

A value 70 of the accumulated engine out soot threshold 66 is defined for driving profile 62 at response time 67. For driving profile 62, if the soot sensor current threshold 59 of FIG. 5 is reached earlier than the response time 67, an accumulated engine out soot value 71 will be less than the value 70 of the accumulated engine out soot threshold 66, indicating a fault condition as soot accumulated faster than anticipated in the sensor 22 of FIGS. 1 and 2. Conversely for driving profile 62, if the soot sensor current threshold 59 of FIG. 5 is reached later than the response time 67, an accumulated engine out soot value 72 will be greater than the value 70 of the accumulated engine out soot threshold 66, indicating no fault condition.

A value 80 of the accumulated engine out soot threshold 66 is defined for driving profile 63 at response time 68. For driving profile 63, if the soot sensor current threshold 59 of FIG. 5 is reached earlier than the response time 68, an accumulated engine out soot value 81 will be less than the value 80 of the accumulated engine out soot threshold 66, indicating a fault condition as soot accumulated faster than anticipated in the sensor 22 of FIGS. 1 and 2. Conversely for driving profile 63, if the soot sensor current threshold 59 of FIG. 5 is reached later than the response time 68, an accumulated engine out soot value 82 will be greater than the value 80 of the accumulated engine out soot threshold 66, indicating no fault condition.

A value 90 of the accumulated engine out soot threshold 66 is defined for driving profile 64 at response time 69. For driving profile 64, if the soot sensor current threshold 59 of FIG. 5 is reached earlier than the response time 69, an accumulated engine out soot value 91 will be less than the value 90 of the accumulated engine out soot threshold 66, indicating a fault condition as soot accumulated faster than anticipated in the sensor 22 of FIGS. 1 and 2. Conversely for driving profile 64, if the soot sensor current threshold 59 of FIG. 5 is reached later than the response time 69, an accumulated engine out soot value 92 will be greater than the value 90 of the accumulated engine out soot threshold 66, indicating no fault condition.

Figure 7:
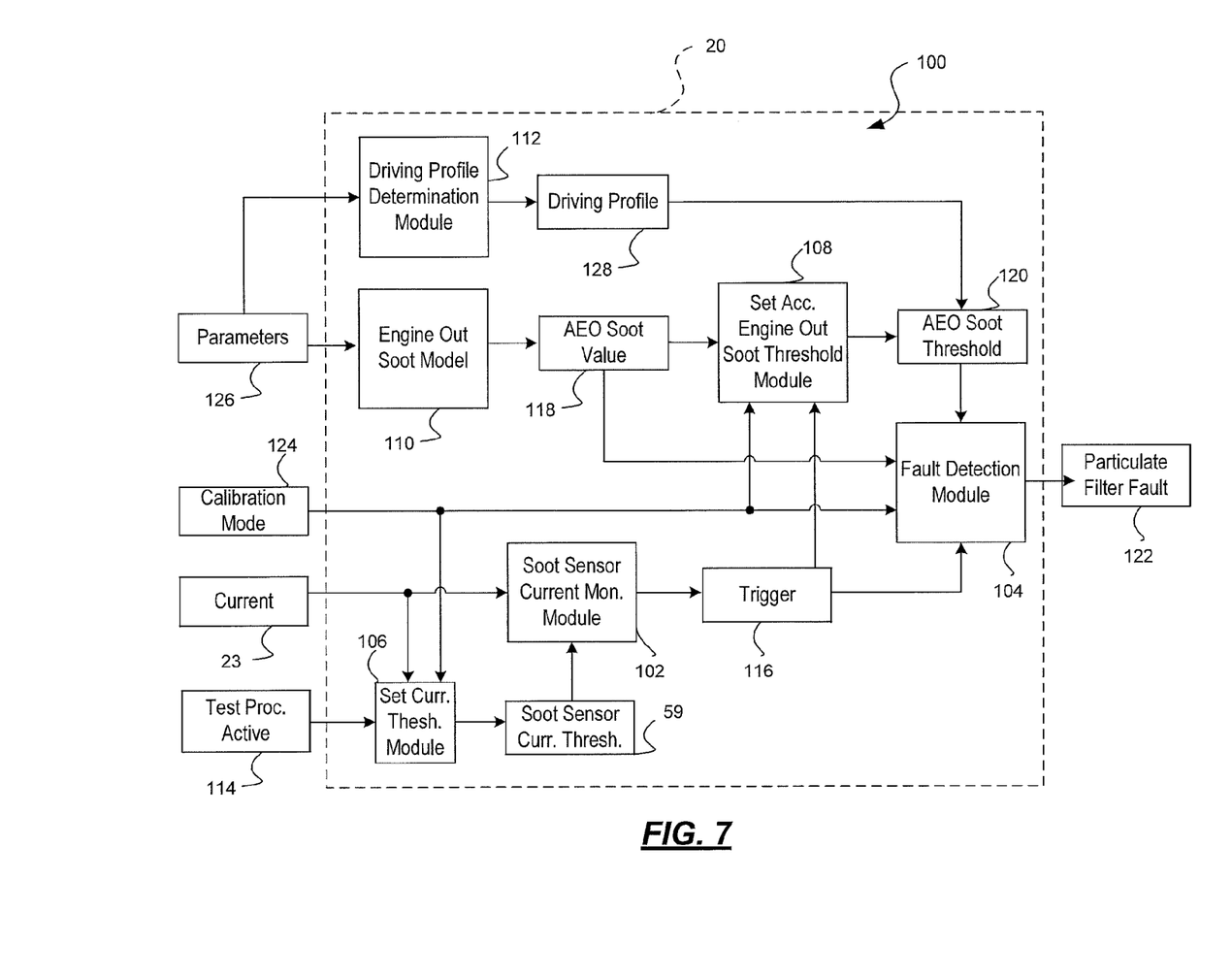
FIG. 7 is a dataflow diagram illustrating a monitoring system of the exhaust gas treatment system of FIG. 1 in accordance with exemplary embodiments.

Referring now to FIG. 7, a dataflow diagram illustrates various embodiments of a monitoring system 100 that may be embedded within the control module 20 of the exhaust gas treatment system 10 of FIGS. 1 and 2. Various embodiments of the monitoring system 100 according to the present disclosure may include any number of sub-modules embedded within the control module 20. As can be appreciated, the sub-modules shown in FIG. 7 may be combined and/or further partitioned. Inputs to the system may be sensed from sensors 22 and 24 of FIGS. 1 and 2 as well as other sensors (not shown) within the vehicle 14, received from other control modules (not shown), and/or determined/modeled by other sub-modules (not shown) within the control module 20. In various embodiments, the monitoring system 100 includes a soot sensor current monitor module 102, a fault detection module 104, a set current threshold module 106, a set accumulated engine out soot threshold module 108, an engine out soot model 110, and a driving profile determination module 112. The modules 102-112 may also be referred to as a first module 102, a second module 104, a third module 106, a fourth module 108, a fifth module 110, and a sixth module 112.

The soot sensor current monitor module 102 is configured to monitor current 23 received from the soot sensor 22 in the exhaust gas treatment system 10 of FIGS. 1 and 2. The set current threshold module 106 also receives the current 23, as well as a test procedure active 114 indication. The set current threshold module 106 may also receive a calibration mode 124. The set current threshold module 106 is configured to set the soot sensor current threshold 59 based on monitoring the current 23 received from the soot sensor 22 while the exhaust gas treatment system 10 includes the emission limit fault version 26 of the particulate filter 18 configured to produce a detectable failure during a test procedure cycle, and the test procedure active 114 indicates that test procedure cycle is active. The soot sensor current threshold 59 may be a maximum current detected during the test procedure cycle while the test procedure active 114 is set.

The calibration mode 124 may be used to indicate whether calibration is active or inactive, where the calibration mode 124 is inactive if the production version 25 (FIG. 1) of the particulate filter 18 is installed, and the calibration mode 124 can be active when the emission limit fault version 26 (FIG. 2) of the particulate filter 18 is installed. The calibration mode 124 can be provided to the fault detection module 104, the set current threshold module 106, and the set accumulated engine out soot threshold module 108. Accordingly, when the calibration mode 124 is active, the modules 104-108 may determine that the exhaust gas treatment system 10 of FIGS. 1 and 2 includes the emission limit fault version 26 of the particulate filter 18, while the calibration mode 124 being inactive is interpreted as the exhaust gas treatment system 10 including the production version 25 of the particulate filter 18.

The soot sensor current monitor module 102 compares the current 23 to the soot sensor current threshold 59, and initiates a trigger 116 based on a determination that the current 23 is greater than or equal to the soot sensor current threshold 59. The fault detection module 104 is configured to compare an accumulated engine out soot value 118 to an accumulated engine out soot threshold 120 in response to the trigger 116, and set a particulate filter fault 122 based on a determination that the accumulated engine out soot value 118 is less than the accumulated engine out soot threshold 120. The comparison of the accumulated engine out soot value 118 to the accumulated engine out soot threshold 120 may be performed while the exhaust gas treatment system 10 includes the production version 25 of the particulate filter 18 of FIG. 1, as indicated by the calibration mode 124. The trigger 116 may also be used to initiate regeneration of the soot sensor 22 of FIGS. 1 and 2.

The set accumulated engine out soot threshold module 108 is configured to set the accumulated engine out soot threshold 120 based on recording a value of the accumulated engine out soot value 118 when the current 23 reaches the soot sensor current threshold 59 as indicated by the trigger 116, while the exhaust gas treatment system 10 includes the emission limit fault version 26 of the particulate filter 18, as indicated by the calibration mode 124. The engine out soot model 110 is configured to generate the accumulated engine out soot value 118, and provide the accumulated engine out soot value 118 to the fault detection module 104 and the set accumulated engine out soot threshold module 108. Therefore, the same engine out soot model 110 can be used to generate the accumulated engine out soot value 118 for setting the accumulated engine out soot threshold 120 and for setting the particulate filter fault 122, although the fault detection module 104 and the set accumulated engine out soot threshold module 108 are operable under different conditions, e.g., based on the calibration mode 124. Using the same engine out soot model 110 for threshold generation and for fault detection results in a relative comparison as the accuracy of the engine out soot model 110 is the same in both instances; therefore, the engine out soot model 110 need not be highly accurate.

The engine out soot model 110 may apply known techniques to determine the accumulated engine out soot value 118 based on engine and exhaust system parameters 126. The engine and exhaust system parameters 126 can be provided by other modules (not depicted) of the control module 20 and may include data from the one or more sensors 24 of the engine 12 of FIGS. 1 and 2 or other engine and exhaust system data sources. The engine and exhaust system parameters 126 may include, for example, engine fuel injection timing, air-fuel ratio, engine speed, and engine torque, as well as other engine parameters.

The accumulated engine out soot threshold 120 may be associated with a driving profile 128. The accumulated engine out soot threshold 120 can be selected for comparison to the accumulated engine out soot value 118 based on the driving profile 128. For example, if the driving profile 128 is omitted, the accumulated engine out soot threshold 120 can be a single value; however, if the driving profile 128 is included, then the accumulated engine out soot threshold 120 can be determined for each driving profile 128 and thus may be formatted as a vector or table for use by the fault detection module 104. The example of FIG. 6 illustrates multiple driving profiles 62-64 having different values 60, 70, and 80 for the accumulated engine out soot threshold 66, where the accumulated engine out soot threshold 66 is a multi-value example of the accumulated engine out soot threshold 120 of FIG. 7.

The driving profile determination module 112 may determine the driving profile 128 or multiple driving profiles 128 based on the engine and exhaust system parameters 126. Parameters such as engine load, power, and/or exhaust temperature can be used to define and distinguish between the driving profiles 128. The driving profiles 128 may be identified when setting the accumulated engine out soot threshold 120 and when using the accumulated engine out soot threshold 120 for fault determination.

Figure 8:
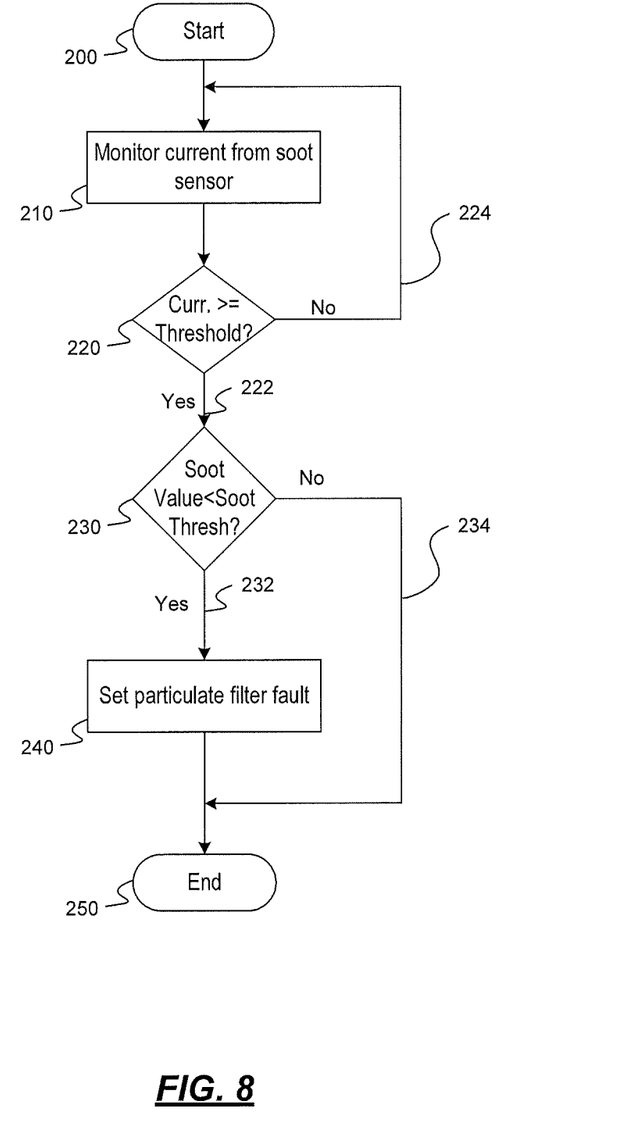
FIG. 8 is a flowchart illustrating a method that may be performed by the monitoring system of FIG. 7 in accordance with exemplary embodiments.

Referring now to FIG. 8, and with continued reference to FIGS. 1-7, a flowchart illustrates a method for particulate filter performance monitoring of an exhaust gas treatment system that can be performed by the monitoring system 100 of FIG. 7 in accordance with the present disclosure. As can be appreciated in light of the disclosure, the order of operation within the method is not limited to the sequential execution as illustrated in FIG. 8, but may be performed in one or more varying orders as applicable and in accordance with the present disclosure. In various embodiments, the method can be scheduled to run based on predetermined events, and/or run continually during operation of the engine 12.

In one example, the method may begin at block 200. At block 210, the soot sensor current monitor module 102 of the monitoring system 100 monitors a current 23 received from a soot sensor 22 in the exhaust gas treatment system 10. At block 220, the soot sensor current monitor module 102 compares the current 23 to a soot sensor current threshold 59. Based on determining that the current 23 is greater than or equal to the soot sensor current threshold 59, the method continues at 222 to block 230; otherwise, at 224 the method returns to block 210. An indication that the current 23 is greater than or equal to the soot sensor current threshold 59 may be embodied as trigger 116.

At block 230, the fault detection module 104 of the monitoring system 100 compares an accumulated engine out soot value 118 to an accumulated engine out soot threshold 120. The comparison can be based on the trigger 116. Comparing of the accumulated engine out soot value 118 to the accumulated engine out soot threshold 120 can be performed while the exhaust gas treatment system 10 includes the production version 25 of the particulate filter 18, which may be indicated by the calibration mode 124 being inactive or cleared. Based on determining that the accumulated engine out soot value 118 is less than the accumulated engine out soot threshold 120, the method continues at 232 to block 240; otherwise, at 234 the method ends at block 250.

At block 240, the fault detection module 104 sets a particulate filter fault 122. The particulate filter fault 122 indicates a fault condition with the particulate filter 18, such as a loss of filter efficiency of the filter media 19. Thereafter, the method may end at block 250.

As previously described, the soot sensor current threshold 59 can be set based on monitoring the current 23 received from the soot sensor 22 while the exhaust gas treatment system 10 includes the emission limit fault version 26 of the particulate filter 18 configured to produce a detectable failure during a test procedure cycle. When the calibration mode 124 is active or set, this can indicate that the emission limit fault version 26 of the particulate filter 18 is installed, and the test procedure active 114 can indicate when a test procedure cycle is active. Once the soot sensor current threshold 59 is set, a subsequent test procedure cycle may be performed to set the accumulated engine out soot threshold 120 based on recording a value of the accumulated engine out soot value 118 when the current 23 reaches the soot sensor current threshold 59 while the exhaust gas treatment system 10 still includes the emission limit fault version 26 of the particulate filter 18. Additional test procedure cycles can be run that correspond to different driving profiles 128 to record multiple values of the accumulated engine out soot threshold 120 associated with the driving profiles 128. When the method of FIG. 8 is performed with multiple driving profiles 128, block 230 may select the accumulated engine out soot threshold 120 for comparing to the accumulated engine out soot value 118 based on a corresponding driving profile 128.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed, but that the invention will include all embodiments falling within the scope of the application.

What is claimed is:

1. A method for particulate filter performance monitoring in an exhaust gas treatment system, comprising:
    monitoring, by a monitoring system comprising processing circuitry, a current received from a soot sensor in the exhaust gas treatment system;
    comparing, by the monitoring system, the current to a soot sensor current threshold;
    associating an accumulated engine out soot threshold with a driving profile;
    selecting, by the monitoring system, the accumulated engine out soot threshold based on the driving profile;
    based on determining that the current is greater than or equal to the soot sensor current threshold, comparing an accumulated engine out soot value to the accumulated engine out soot threshold by the monitoring system; and
    based on determining that the accumulated engine out soot value is less than the accumulated engine out soot threshold, setting a particulate filter fault by the monitoring system.

2. The method of claim 1 wherein the comparing of the accumulated engine out soot value to the accumulated engine out soot threshold is performed while the exhaust gas treatment system includes a production version of a particulate filter.

3. The method of claim 1 further comprising:
    setting the soot sensor current threshold based on monitoring the current received from the soot sensor while the exhaust gas treatment system includes an emission limit fault version of the particulate filter configured to produce a detectable failure during a test procedure cycle.

4. The method of claim 3 further comprising:
    setting the accumulated engine out soot threshold based on recording a value of the accumulated engine out soot value when the current reaches the soot sensor current threshold while the exhaust gas treatment system includes the emission limit fault version of the particulate filter.

5. The method of claim 4 further comprising:
    determining the accumulated engine out soot value based on an engine out soot model, wherein the engine out soot model generates the accumulated engine out soot value for setting the accumulated engine out soot threshold and for setting the particulate filter fault.

6. A monitoring system for an exhaust gas treatment system, comprising:
    processing circuitry and a non-transitory machine-readable storage medium comprising instructions executable by the processing circuitry to:
    monitor a current received from a soot sensor in the exhaust gas treatment system, compare the current to a soot sensor current threshold, and initiate a trigger based on a determination that the current is greater than or equal to the soot sensor current threshold; and
    compare an accumulated engine out soot value to an accumulated engine out soot threshold in response to the trigger, and set a particulate filter fault based on a determination that the accumulated engine out soot value is less than the accumulated engine out soot threshold, wherein the accumulated engine out soot threshold is associated with a driving profile, and the accumulated engine out soot threshold is selected for comparison to the accumulated engine out soot value based on the driving profile.

7. The monitoring system of claim 6 wherein the comparison of the accumulated engine out soot value to the accumulated engine out soot threshold is performed while the exhaust gas treatment system includes a production version of a particulate filter.

8. The monitoring system of claim 6 wherein the non-transitory machine-readable storage medium further comprises instructions executable by the processing circuitry to set the soot sensor current threshold based on monitoring the current received from the soot sensor while the exhaust gas treatment system includes an emission limit fault version of the particulate filter configured to produce a detectable failure during a test procedure cycle.

9. The monitoring system of claim 8 wherein the non-transitory machine-readable storage medium further comprises instructions executable by the processing circuitry to set the accumulated engine out soot threshold based on recording a value of the accumulated engine out soot value when the current reaches the soot sensor current threshold while the exhaust gas treatment system includes the emission limit fault version of the particulate filter.

10. The monitoring system of claim 9 further comprising an engine out soot model that generates the accumulated engine out soot value.

11. The monitoring system of claim 8 wherein the soot sensor current threshold is a maximum current detected during the test procedure cycle.

12. An exhaust gas treatment system of an engine, comprising:
   a particulate filter;
   a soot sensor configured to output a current related to an amount of soot over a period of time in an exhaust path downstream of the particulate filter; and
   a monitoring system configured to compare the current to a soot sensor current threshold, initiate a trigger based on a determination that the current is greater than or equal to the soot sensor current threshold, compare an accumulated engine out soot value to an accumulated engine out soot threshold in response to the trigger, and set a particulate filter fault based on a determination that the accumulated engine out soot value is less than the accumulated engine out soot threshold, wherein the soot sensor current threshold is a maximum current detected during a test procedure cycle.

13. The exhaust gas treatment system of claim 12 wherein the comparison of the accumulated engine out soot value to the accumulated engine out soot threshold is performed while the exhaust gas treatment system includes a production version of the particulate filter.

14. The exhaust gas treatment system of claim 12 wherein the monitoring system is further configured to set the soot sensor current threshold based on monitoring the current received from the soot sensor while the exhaust gas treatment system includes an emission limit fault version of the particulate filter configured to produce a detectable failure during the test procedure cycle.

15. The exhaust gas treatment system of claim 14 wherein the monitoring system is further configured to set the accumulated engine out soot threshold based on recording a value of the accumulated engine out soot value when the current reaches the soot sensor current threshold while the exhaust gas treatment system includes the emission limit fault version of the particulate filter.

16. The exhaust gas treatment system of claim 15 wherein the monitoring system further comprises an engine out soot model configured to generate the accumulated engine out soot value for setting the accumulated engine out soot threshold and for setting the particulate filter fault.

17. The exhaust gas treatment system of claim 15 wherein the accumulated engine out soot threshold is associated with a driving profile, and the accumulated engine out soot threshold is selected for comparison to the accumulated engine out soot value based on the driving profile.

* * * * *